US00PP16169P2

(12) United States Plant Patent
Hammett

(10) Patent No.: US PP16,169 P2
(45) Date of Patent: Dec. 20, 2005

(54) ***NEMESIA* PLANT NAMED 'NEMROWHI'**

(50) Latin Name: *Nemesia caerula*
Varietal Denomination: Nemrowhi

(75) Inventor: Keith Richard William Hammett, Massey (NZ)

(73) Assignee: Seaview Nurseries Ltd., Manurewa (NZ)

( * ) Notice: Subject to any disclaimer, the term of this patent is extended or adjusted under 35 U.S.C. 154(b) by 0 days.

(21) Appl. No.: 10/818,348

(22) Filed: Apr. 5, 2004

(51) Int. Cl.[7] ..... A01H 5/00
(52) U.S. Cl. ..... Plt./263
(58) Field of Search ..... Plt./263

*Primary Examiner*—Howard J. Locker
(74) *Attorney, Agent, or Firm*—C. A. Whealy

(57) ABSTRACT

A new and distinct cultivar of *Nemesia* plant named 'Nemrowhi', characterized by its compact, upright and somewhat outwardly spreading plant habit; freely branching habit; and numerous violet and white bi-colored flowers.

1 Drawing Sheet

Botanical classification/cultivar denomination: *Nemesia caerula* cultivar Nemrowhi.

BACKGROUND OF THE INVENTION

The present invention relates to a new and distinct cultivar of *Nemesia* plant, botanically known as *Nemesia caerula* and referred to by the name 'Nemrowhi'.

The new *Nemesia* is a product of a planned breeding program conducted by the Inventor in Auckland, New Zealand. The objective of the program is to create new compact *Nemesia* cultivars with numerous flowers and unique flower colors.

The new *Nemesia* originated from a cross-pollination by the Inventor of a proprietary *Nemesia caerula* selection identified as code number 651/07, not patented, as the female, or seed, parent with a proprietary *Nemesia caerula* selection identified as code number 682/01, not patented, as the male, or pollen, parent on Oct. 5, 1999. The cultivar Nemrowhi was discovered and selected by the Inventor as a flowering plant within the progeny of the stated cross-pollination in a controlled environment in Auckland, New Zealand on Apr. 2, 2000.

Asexual reproduction of the new *Nemesia* by terminal cuttings in a controlled environment in Auckland, New Zealand since April, 2000, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature and light intensity, without, however, any variance in genotype.

The following characteristics have been repeatedly observed and are determined to be basic characteristics of 'Nemrowhi' and distinguish 'Nemrowhi' as a new and distinct cultivar:

1. Compact, upright and somewhat outwardly spreading plant habit.
2. Freely branching habit.
3. Numerous violet and white bi-colored flowers.

Plants of the new *Nemesia* are more compact and more uniform in plant habit than plants of the parent selections. In addition, plants of the new *Nemesia* and the male parent selection differ in flower coloration as plants of the male parent selection have pink and white bi-colored flowers.

Plants of the new *Nemesia* can be compared to plants of the cultivar Innkapink, disclosed in U.S. Plant Pat. No. 14,660. In side-by-side comparisons conducted in Auckland, New Zealand, plants of the new *Nemesia* differed from plants of the cultivar Innkapink in the following characteristics:

1. Plants of the new *Nemesia* were more upright than plants of the cultivar Innkapink.
2. Plants of the new *Nemesia* and the cultivar Innkapink differed in flower color as plants of the cultivar Innkapink had pink-colored flowers.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia.*

The photograph at the top of the sheet comprises a side perspective view of a typical plant of 'Nemrowhi' grown in a container.

The photograph at the bottom of the sheet comprises a close-up view of typical flowers of 'Nemrowhi'.

DETAILED BOTANICAL DESCRIPTION

The aforementioned photographs and following observations and averaged measurements describe plants grown in Encinitas, Calif., in a polyethylene-covered greenhouse during the spring with day temperatures about 24° C., night temperatures about 19° C. and light levels about 4,000 foot-candles. Plants were grown for 15 weeks in one-gallon containers with three plants per container. Plants were pinched once about five weeks after planting. Color references are made to The Royal Horticultural Society Colour Chart except where general terms of ordinary dictionary significance are used.

Botanical classification: *Nemesia caerula* cultivar Nemrowhi.

Parentage:

*Female parent*.—Proprietary *Nemesia caerula* selection identifies as code number 651/07, not patented.

*Male parent*.—Proprietary *Nemesia caerula* selection identifies as code number 682/01, not patented.

Propagation:

*Type*.—By vegetative cuttings.

*Time to initiate roots, summer*.—About 10 days at 20° C.

*Time to initiate roots, winter*.—About 15 days at 15° C.

*Time to develop roots, summer*.—About 33 days at 20° C.

*Time to develop roots, winter*.—About 35 days at 15° C.

*Root description*.—Fibrous, fine; white in color.

*Rooting habit*.—Freely branching.

Plant description:

*General appearance*.—Compact, upright and somewhat outwardly spreading plant habit. Freely branching, typically about six primary laterals with numerous secondary laterals developing after pinching. Numerous violet and white bi-colored zygomorphic flowers. Moderately vigorous growth habit.

*Plant height*.—About 29 cm.

*Plant diameter or spread, single plant*.—About 18 cm.

*Lateral branches*.—Appearance: Square in cross-section; wiry. Length: About 29 cm. Diameter: About 3 mm. Internode length: About 2.5 cm. Strength: Strong; rigid. Texture: Glabrous. Color: 144A.

*Foliage description*.—Arrangement: Opposite, simple. Shape: Lanceolate. Apex: Acute. Base: Obtuse to slightly attenuate. Length: About 2.7 cm. Width: About 1.4 cm. Margin: Serrate. Texture, upper and lower surfaces: Glabrous, smooth. Venation pattern: Pinnate, arcuate. Petiole length: About 2.5 mm. Petiole diameter: About 2 mm. Color: Developing and fully expanded leaves, upper surface: 146A. Developing and fully expanded leaves, lower surface: 146B. Venation, upper surface: 146A. Venation, lower surface: 146B. Petiole, upper and lower surfaces: 146B.

Flowering description:

*Arrangement/appearance*.—Zygomorphic and personate solitary flowers arranged on terminal racemes; flowering acropetally towards apex. Flowers bilabiate with nectar spur. Flowers face mostly outward. Flowers last about five days on the plant. Flowers not persistent.

*Natural flowering season*.—Natural flowering season is spring to fall; flowering continuous during this period.

*Quantity of flowers*.—Freely flowering with about 16 flowers and flower buds per raceme at one time.

*Fragrance*.—Faint; sweet floral.

*Inflorescence length*.—About 14 cm.

*Inflorescence diameter*.—About 3.5 cm.

*Flower height*.—About 1.8 cm.

*Flower width*.—About 1.5 cm.

*Flower depth, including nectar spur*.—About 1.6 cm.

*Nectar spur length*.—About 7 mm.

*Flower buds*.—Shape: Ovoid with spur. Length: About 9 mm. Diameter: About 4 mm. Color: 85B.

*Petals*.—Arrangement/shape: Five petals total. Four upper petals are fused at base to form an upright lobed and arched banner lip; lower petal modified into a larger lip with nectar spur and convex oval protuberance which serves as pollinator nectar guide and landing platform. Apex: Rounded. Margin: Entire. Length: Upper lip petals: About 6 mm. Lower lip petal: About 7 mm. Width: Upper lip petals: Lateral two petals: About 6 mm. Center two petals: About 3 mm. Lower lip petal: About 9 mm. Texture: Smooth, velvety. Color: When opening, upper lip petals, upper surface: 77B; towards the base, 83B. When opening, lower lip petal, upper surface: 69C. When opening, all petals, lower surface: 69A. Fully opened, upper lip petals, upper surface: 85A; towards the base, 86A; color becoming closer to 85C to 85D to nearly white with development. Fully opened, lower lip petal, upper surface: 155D tinged with 85C; color becoming white, close to 155D, with development. Fully opened, lower surface: 85C to 85D. Nectar guide, when opening: 5A. Nectar guide, fully opened: 14A.

*Sepals*.—Quantity: Five-parted, star-shaped calyx. Shape: Elliptic. Apex: Acute. Base: Fused. Margin: Entire. Length: About 3 mm. Diameter: About 1 mm. Texture, upper and lower surfaces: Smooth. Color, upper and lower surfaces: 146B.

*Peduncle*.—Length: About 4 to 5.7 cm. Diameter: About 1.5 mm. Strength: Strong. Angle: Upright to 45° from the stem. Color: 144A.

*Pedicel*.—Length: About 1.2 cm. Diameter: Less than 1 mm. Strength: Slender, but hold flowers outward. Angle: About 45° from the stem. Color: 144A.

*Androecium*.—Stamen number: Four per flower. Anther shape: Oval. Anther size: Less than 1 mm. Anther color: 12A. Amount of pollen: Scarce. Pollen color: 12A.

*Gynoecium*.—Pistil number: One per flower. Pistil length: About 2 mm. Style length: About 1 mm. Style color: 157C. Stigma shape: Rounded. Stigma color: 157C. Ovary color: 145A.

*Seed/fruit*.—Seed and fruit production has not been observed on plants of the new *Nemesia*.

Disease/pest resistance: Plants of the new *Nemesia* have not been observed to be resistant to pathogens or pests common to *Nemesias*.

Temperature tolerance: Plants of the new *Nemesia* have been observed to be tolerant to temperatures ranging from 4° to 32° C.

It is claimed:

1. A new and distinct cultivar of *Nemesia* plant named 'Nemrowhi', as illustrated and described.

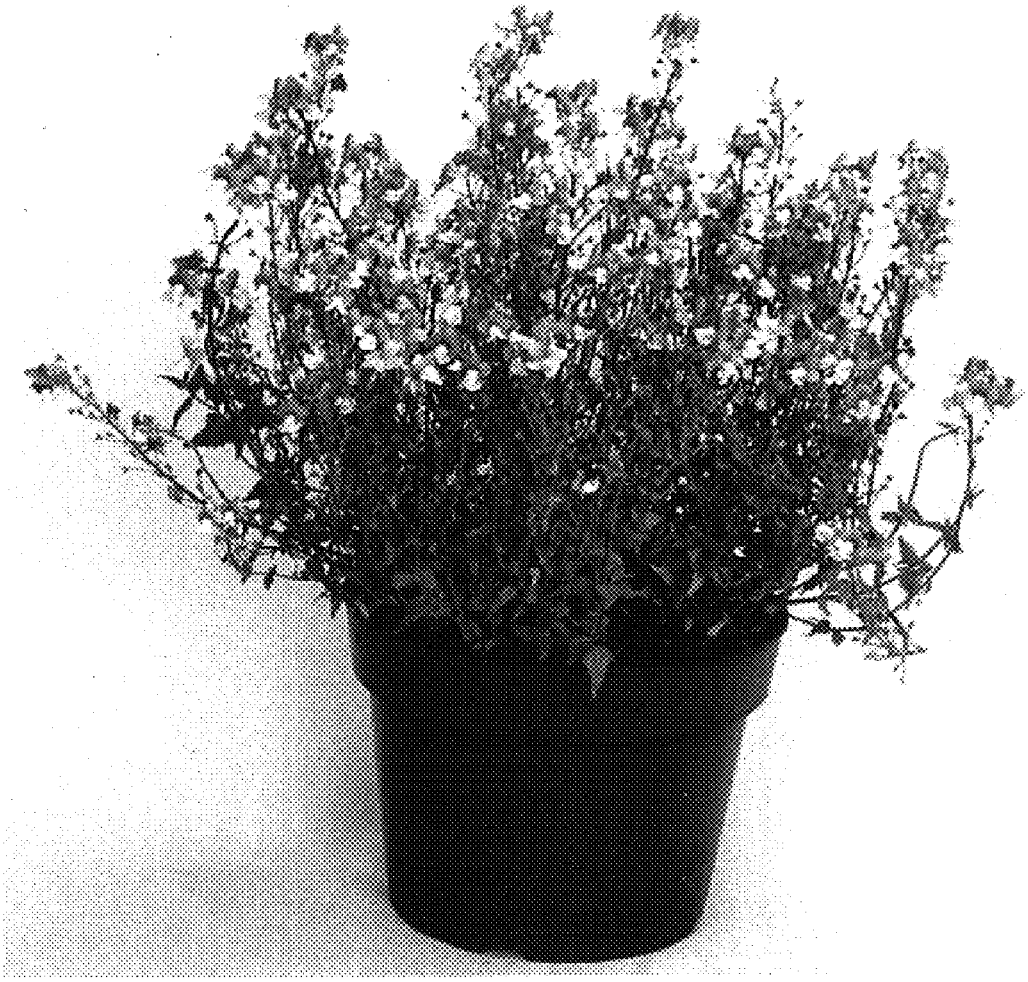
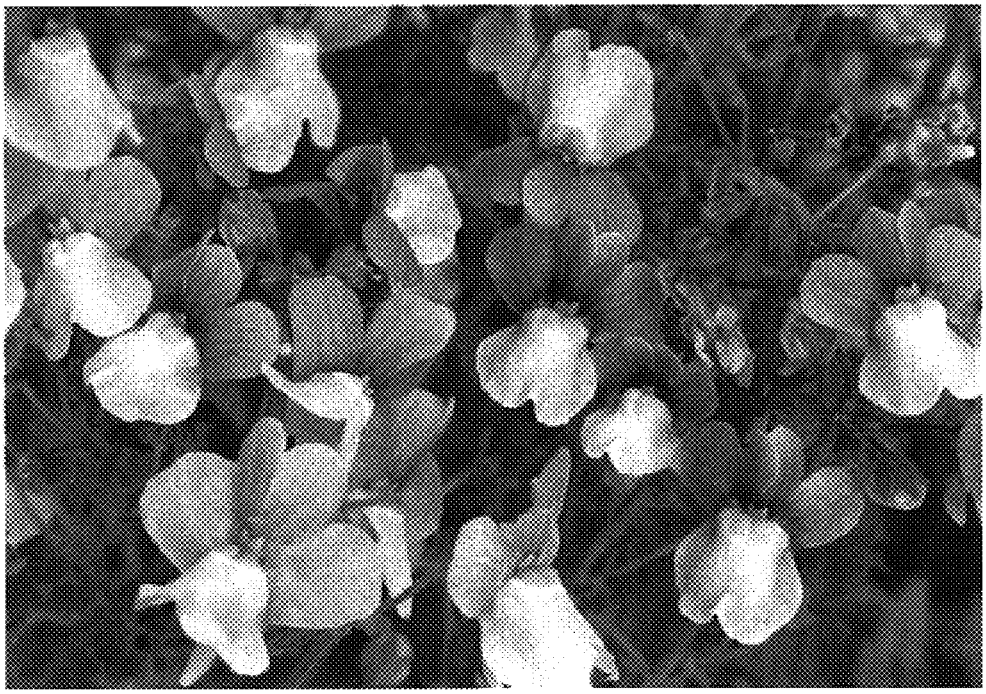

* * * * *